United States Patent [19]

Münster et al.

[11] Patent Number: 5,543,416
[45] Date of Patent: Aug. 6, 1996

[54] CYANOISOXAZOLES

[75] Inventors: Peter Münster, Neulussheim; Klaus Ditrich, Gönnheim; Gerhard Hamprecht, Weinheim; Matthias Gerber, Limburgerhof; Karl-Otto Westphalen, Speyer; Helmut Walter, Obrigheim; Rudolf Karl, Mutterstadt, all of Germany

[73] Assignee: BASF Aktiengesellschaft, Ludwigshafen, Germany

[21] Appl. No.: 392,330

[22] Filed: Feb. 22, 1995

[30] Foreign Application Priority Data

Feb. 25, 1994 [DE] Germany .................. 44 06 209.5

[51] Int. Cl.$^6$ .................. A01N 43/72; C07D 261/06
[52] U.S. Cl. .................. 504/271; 548/248
[58] Field of Search .................. 548/248; 504/271

[56] References Cited

FOREIGN PATENT DOCUMENTS

| 002881 | 7/1979 | European Pat. Off. . |
| 337263 | 10/1990 | European Pat. Off. . |
| 418667 | 3/1991 | European Pat. Off. . |
| 503410 | 9/1992 | European Pat. Off. . |
| 92/16514 | 10/1992 | WIPO . |

OTHER PUBLICATIONS

Camparini et al., *J. of the Chem. Society*, No. 7, Jul. 1982, pp. 2391–2394.
Camparini et al., *J. of Heterocyclic Chemistry*, vol. 22, No. 5, 1985, pp. 1561–1565.
Westphal et al., *Zeitschrift für Chemie*, vol. 22, No. 4, Apr. 1982, pp. 138–139.

*Primary Examiner*—Joseph K. McKane
*Attorney, Agent, or Firm*—Keil & Weinkauf

[57] ABSTRACT

Cyanoisoxazoles of the formula Ia or Ib where $R^1$ is hydrogen, alkyl, cycloalkyl, phenyl; $R^2$ is hydrogen, alkyl, cycloalkyl and $R^3$ is alkoxy, alkyl, cycloalkyl, cycloalkenyl, alkenyl, alkynyl or phenyl, it being possible for the organic radicals mentioned under $R^1$, $R^2$ and $R^3$ to be substituted in each case. The compounds of the Formula Ia or Ib are useful as herbicides.

3 Claims, 1 Drawing Sheet

CYANOISOXAZOLES

The present invention relates to cyanoisoxazoles of the general formula Ia or Ib Ia Ib where the substituents have the following meanings:

$R^1$ is hydrogen;

$C_1$–$C_6$-alkyl which can carry one to five halogen atoms and/or one cyano radical and/or up to two of the following radicals: $C_1$–$C_4$-alkoxy, $C_1$–$C_4$-haloalkoxy, $C_1$–$C_4$-alkylthio, $C_1$–$C_4$-haloalkylthio, $C_3$–$C_6$-cycloalkyl, which in turn can be substituted by one to three halogen or $C_1$–$C_4$-alkyl radicals or phenyl which can additionally carry one to three of the following radicals: cyano, halogen, nitro, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio;

$C_3$–$C_8$-cycloalkyl which can be substituted one to three times by $C_1$–$C_4$-alkyl and/or halogen;

phenyl which can additionally carry one to three of the following radicals: cyano, nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio;

$R^2$ is hydrogen (particularly preferred);

$C_1$–$C_6$-alkyl which can carry one to three of the following substituents: hydroxyl, halogen, $C_1$–$C_4$-alkoxy and/or $C_1$–$C_4$-alkylthio;

$C_3$–$C_8$-cycloalkyl which can be substituted one to three times by halogen, $C_1$–$C_4$-alkyl and/or $C_1$–$C_4$-haloalkyl;

$R^3$ is a $C_1$–$C_4$-alkoxy group;

a $C_1$–$C_6$-alkyl group which can carry one to three of the following radicals: halogen, cyano, $C_1$–$C_4$-alkoxy, $C_1$–$C_4$-haloalkoxy, $C_1$–$C_4$-alkylthio, $C_1$–$C_4$-haloalkylthio, $C_3$–$C_8$-cycloalkyl or phenyl, it being possible for the phenyl ring in turn to carry one to three of the following radicals: halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and/or $C_1$–$C_4$-haloalkylthio;

a $C_3$–$C_6$-cycloalkenyl group which can be substituted one to three times by halogen or $C_1$–$C_4$-alkyl;

a $C_3$–$C_8$-cycloalkyl group which can carry one to three of the following radicals: halogen, nitro, cyano, $C_1$–$C_6$-alkyl, $C_1$–$C_6$-haloalkyl, $C_1$–$C_4$-alkoxy and/or $C_1$–$C_4$-haloalkoxy;

a $C_3$–$C_6$-alkenyl or $C_3$–$C_6$-alkynyl group which in each case can be substituted one to three times by halogen and/or once by phenyl, it being possible for the phenyl radical in turn to carry one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro;

the phenyl group, which can additionally carry one to three of the following radicals: cyano, nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio and/or $C_1$–$C_6$-haloalkylthio.

The invention additionally relates to herbicidal compositions which contain the compounds Ia and/or Ib as active substances and processes for preparing these substances.

Herbicidally active isoxazolecarboxamides have been disclosed, eg. in EP-A-337 263, EP-A-418 667, EP-A-503 410 and WO 92/16514. In spite of the good herbicidal activity per se of these compounds, it was the object to synthesize similar compounds having improved ecobiological properties, in particular more lipophilic compounds in comparison with the free carboxylic acids disclosed in the specifications cited above.

Accordingly, the cyanoisoxazoles Ia and Ib defined at the outset have been found.

The carboxamides of the formula Ia or Ib according to the invention can be prepared by the following two routes:

Route 1:

A process for synthesizing the isoxazolecarboxamides Ia according to the invention, where $R^1$, $R^2$ and $R^3$ have the abovementioned meanings, consists in converting an isoxazolecarboxylic acid of the formula II to a carboxylic acid halide X or another activated form of the carboxylic acid (A) in a manner known per se and then converting with ammonia to the amide III (B), which can be converted by reaction with dehydrating agents to a nitrile of the formula Ia (C).

The isoxazolecarboxylic acids required for this process are known.

In addition to halides such as, in particular, the chlorides and the bromides, activated forms of the carboxylic acid are, for example, also imidazolides. In general, the halides are preferred.

They are obtained by reaction of the carboxylic acids II with a halogenating agent such as thionyl chloride, thionyl bromide, phosgene, phosphorus oxychloride or phosphorus oxybromide, phosphorus tri- and pentachloride or phosphorus tri- and pentabromide and also elemental chlorine and bromine.

The halogenating agent is employed in an amount of from 1 to 5 mole equivalents, preferably from 1 to 4 mole equivalents.

The reaction proceeds at from 20° C. up to the boiling point of the halogenating agent or, if the reaction is carried out in the presence of an inert organic solvent, alternatively at its boiling point.

Suitable solvents are, for example, hydrocarbons and halohydrocarbons such as benzene, toluene and dichloromethane.

The activated carboxylic acid derivatives are customarily isolated, for example by distilling off the halogenating agent and the solvent if present, and only then reacting with ammonia.

In this case, the amidation is carried out at from −20° to 50° C., preferably from 0° to 30° C., in an inert aprotic polar organic solvent.

Suitable solvents for this reaction are, in particular, halohydrocarbons, such as dichloromethane, and ethers such as diethyl ether and tert-butyl methyl ether.

As hydrogen halide is formed in the amidation of acid halides, it is recommended to add ammonia in an excess, based on the starting substance, eg. in amounts of from 2 to 5, preferably from 2 to 3, mole equivalents.

Suitable dehydrating agents for the second reaction step are, inter alia, reagents known from the literature, such as $PCl_3$, $PCl_5$, $POCl_3$, $SOCl_2$, $P_2O_5$, acetic anhydride or trifluoroacetic anhydride. The reaction can be carried out undiluted or in solution. Suitable solvents can be: ethers such as diethyl ether, tert-butyl methyl ether, tetrahydrofuran or dioxane, halogenated hydrocarbons such as, in particular, methylene chloride or 1,2-dichloroethane, aliphatic or aromatic hydrocarbons or even dimethylformamide.

The reaction can be carried out in a temperature range of from −20° C. up to the boiling point of the reaction solution. The dehydrating agents are employed in equimolar amounts or in an excess, based on the diamide.

In a completely similar manner, the compounds Ib according to the invention are accessible according to the following reaction scheme.

Route 2a:

Another process for synthesizing the compounds Ib consists in hydrolyzing an isoxazole-4,5-dicarboxylic acid ester of the formula VI in a manner known per se to the monoester VII, reacting this after activation to give the amide VIII, then after a further hydrolysis step converting the acid IX to the diamide V, which is then converted to the nitrile Ib.

The reaction steps B, C and G can be carried out similarly to the conditions described above in route 1. The reaction E is carried out according to the conditions described in process 1, but advantageously with the proviso that the activating agent, if it can simultaneously also be used as a dehydrating agent, is only employed in a ratio from 0.95 to 1.2 mole equivalents.

The reaction step A is customarily carried out by treating a dialkyl dicarboxylate VI at from 0° to 80° C., preferably from 0° to 40° C., in an organic solvent, eg. methanol or ethanol, with a strong base, eg. an alkali metal or alkaline earth metal hydroxide such as NaOH, KOH or $Ca(OH)_2$. In general, about 1 equivalent (eg. from 0.8 to 1.05 eq.) of the base in aqueous solution is employed here. After reaction has taken place, the mixture is cooled and acidified with a strong acid, eg. a mineral acid such as hydrochloric acid or sulfuric acid. The resultant carboxylic acid VII can be isolated in a customary manner, eg. by filtering off with suction or by extracting with an organic solvent.

The second ester hydrolysis (reaction step D) can be performed in a similar manner, where it may be advantageous to employ the base in an up to 5-fold excess.

The carboxamides X are obtained from the carboxylic acid halides (reaction step F) by reaction with an amine XIV. A procedure is expediently used here in which the carboxylic acid halide is reacted in an inert organic solvent such as dichloroethane, or an ether such as diethyl ether or methyl tert-butyl ether, with an amine XIV advantageously likewise dissolved in an organic solvent. In this process, the amine is expediently employed in a from 2- to 5-fold molar amount, preferably a from 2- to 3-fold molar amount, to bind the resultant hydrogen halide. The reaction can also be carried out in the presence of an auxiliary base such as a tertiary amine, eg. triethylamine. In this case, from 1 to 1.5 mole equivalents of amine XIV suffice. The reaction temperature can be from 0° to 50° C., preferably from 0° to 20° C. In general, the reaction is complete after 1 to 12 hours. The mixture can be worked up in the customary manner, for example by hydrolysis with water and extraction of the diamide V with an organic solvent and concentration of the organic solvent. For purification, the diamide V can be recrystallized or chromatographed, for example.

Route 2b:

A modified process for synthesizing the compounds Ib consists in treating an amide of the formula IX with an up to 10-fold molar excess of thionyl chloride in an inert organic solvent such as eg. toluene or in thionyl chloride as solvent. The reaction can be carried out at from 0° C. up to the boiling point of the mixture. The acid chloride XV thus obtained can then be reacted with an amine XIV as described above in (F) to give the product Ib.

With respect to the herbicidal action according to the invention with, at the same time, good ecobiological behavior, eg. degradability in the soil, the substituents in the compounds Ia and Ib have, for example, the following meanings:

$R^1$ is hydrogen;

unbranched or branched $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-l-methylpropyl and 1-ethyl-2-methylpropyl, in particular methyl, ethyl, propyl, 1-methylethyl and 1,1-dimethylethyl, which can carry one to five halogen atoms such as fluorine, chlorine, bromine, iodine, in particular fluorine and chlorine, and/or a cyano radical and/or up to two of the following radicals:

$C_1$–$C_4$-alkoxy such as methoxy, ethoxy, propoxy, 1-methylethoxy, butoxy, 1-methylpropoxy, 2-methylpropoxy and 1,1-dimethylethoxy, in particular methoxy, ethoxy, 1-methylethoxy and 1,1-dimethylethoxy;

partly or completely halogenated $C_1$–$C_4$-alkoxy such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, in particular trifluoromethoxy and pentafluoroethoxy;

$C_1$–$C_4$-alkylthio such as methylthio, ethylthio, propylthio, 1-methylethylthio, n-butylthio, 1-methylpropylthio, 2-methylpropylthio and 1,1-dimethylethylthio, in particular methylthio and ethylthio;

partly or completely halogenated $C_1$–$C_4$-alkylthio such as difluoromethylthio, trifluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio and pentafluoroethylthio, in particular trifluoromethylthio and pentafluoroethylthio;

a $C_3$–$C_8$-cycloalkyl group such as cyclopropyl, cyclobutyl, cyclopentyl, cyclohexyl, cycloheptyl and cyclooctyl, in particular cyclopropyl, cyclopentyl and cyclohexyl, it being possible for the cyclic system to be additionally substituted one to three times by $C_1$–$C_4$-alkyl as mentioned above, in particular methyl and ethyl; or halogen such as fluorine, chlorine, bromine and iodine, in particular fluorine and chlorine;

the phenyl group which can additionally carry one to three of the following radicals: cyano; nitro; halogen such as fluorine, chlorine, bromine and iodine, in particular fluorine and chlorine; $C_1$–$C_6$-alkyl such as mentioned above, in particular methyl, ethyl and 1-methylethyl; partly or completely halogenated $C_1$–$C_6$-alkyl as mentioned above, in particular trifluoromethyl and chlorodifluoromethyl; $C_1$–$C_6$-alkoxy as mentioned above, in particular methoxy and ethoxy; partly or completely halogenated $C_1$–$C_6$-alkoxy as mentioned above, in particular trifluoromethoxy, trichloromethoxy and pentafluoroethoxy; $C_1$–$C_4$-alkylthio as mentioned above, in particular methylthio and ethylthio, and/or partly or completely halogenated $C_1$–$C_6$-alkylthio as mentioned above, in particular difluoromethylthio, trifluoromethylthio and pentafluoromethylthio;

$R^1$ is furthermore a $C_3$–$C_8$-cycloalkyl group such as cyclopropyl, cyclobutyl, cyclopentyl, cyclohexyl, cycloheptyl and cyclooctyl, in particular cyclopropyl, cyclopentyl and cyclohexyl, it being possible for the cyclic system to be additionally substituted one to three times by $C_1$–$C_4$-alkyl as mentioned above, in particular methyl and ethyl; or halogen such as fluorine, chlorine, bromine and iodine, in particular fluorine and chlorine;

$R^1$ is furthermore the phenyl group, which can additionally carry one to three of the following radicals: cyano; nitro; halogen such as fluorine, chlorine, bromine and iodine, in particular fluorine and chlorine; $C_1$–$C_6$-alkyl as mentioned above, in particular methyl, ethyl and 1-methylethyl; partly or completely halogenated $C_1$–$C_6$-alkyl as mentioned above, in particular trifluoromethyl and chlorodifluoromethyl; $C_1$–$C_6$-alkoxy as mentioned above, in particular methoxy and ethoxy; partly or completely halogenated $C_1$–$C_6$-alkoxy as mentioned above, in particular trifluoromethoxy, trichloromethoxy and pentafluoroethoxy; $C_1$–$C_4$-alkylthio as mentioned above, in particular methylthio and ethylthio, and/or partly or completely halogenated $C_1$–$C_6$-alkylthio as mentioned above, in particular difluoromethylthio, trifluoromethylthio and pentafluoromethylthio;

$R^2$ is hydrogen;

$C_1$–$C_6$-alkyl; preferably $C_1$–$C_4$-alkyl such as methyl, ethyl and tert-butyl, which can carry one to three of the following substituents: hydroxyl, halogen, such as fluorine, chlorine or bromine, $C_1$–$C_4$-alkoxy such as methoxy and tert-butoxy, $C_1$–$C_4$-alkylthio such as methylthio and tert-butylthio;

$C_3$–$C_8$-cycloalkyl, preferably $C_5$–$C_6$-cycloalkyl such as cyclopentyl and cyclohexyl, which can be substituted once to three times by halogen such as fluorine, chlorine and bromine, $C_1$–$C_4$-alkyl such as methyl and tert-butyl or partly or completely halogenated $C_1$–$C_4$-alkyl such as fluoromethyl, trifluoromethyl, chlorodifluoromethyl, pentafluoroethyl and 2-chloro-1,1,2-trifluoroethyl;

$R^3$ is $C_1$–$C_4$-alkoxy, as mentioned above, in particular methoxy, ethoxy and isopropoxy;

branched or unbranched $C_1$–$C_6$-alkyl, preferably $C_3$–$C_4$-alkyl, isopropyl and tert-butyl, which can carry one to three of the following radicals: halogen such as fluorine, chlorine and bromine, cyano, $C_1$–$C_4$-alkoxy such as methoxy and tert-butoxy, partly or completely halogenated $C_1$–$C_4$-alkoxy such as fluoromethoxy, trifluoromethoxy, trichloromethoxy, 2-chloro-1,1,2-trifluoroethoxy and pentafluoroethoxy, $C_1$–$C_4$-alkylthio such as methylthio and tert-butylthio, $C_1$–$C_4$-haloalkylthio such as fluoromethylthio, trichloromethylthio, 2-chloro-1,1,2-trifluoroethylthio and pentafluoroethylthio, $C_3$–$C_8$-cycloalkyl, in particular $C_3$–$C_6$-cycloalkyl such as cyclopropyl, cyclopentyl and cyclohexyl or phenyl, it being possible for the phenyl radical in turn to carry one to three of the following groups: halogen such as fluorine, chlorine and bromine, cyano, nitro, $C_1$–$C_4$-alkyl such as methyl and tert-butyl, $C_1$–$C_4$-haloalkyl such as fluoromethyl, trichloromethyl, 2-chloro-1,1,2-trifluoroethyl and pentafluoroethyl, $C_1$–$C_4$-alkoxy such as methoxy and tert-butoxy, partly or completely halogenated $C_1$–$C_4$-alkoxy such as trifluoromethoxy, trichloromethoxy, 2-chloro-1,1,2-trifluoroethoxy and pentafluoroethoxy, $C_1$–$C_4$-alkylthio such as methylthio and tert-butylthio or $C_1$–$C_4$-haloalkylthio such as trifluoromethylthio, trichloromethylthio, 2-chloro-1,1,2-trifluoroethylthio and pentafluoroethylthio;

$R^3$ is furthermore $C_3$–$C_8$-cycloalkyl, preferably $C_3$–$C_6$-cycloalkyl, in particular cyclopropyl, cyclopentyl and cyclohexyl, which in each case can carry one to three of the following radicals: halogen such as fluorine, chlorine and bromine, nitro, cyano, $C_1$–$C_6$-alkyl, preferably $C_1$–$C_4$-alkyl such as methyl and tert-butyl, partly or completely halogenated $C_1$–$C_6$-alkyl, preferably $C_1$–$C_4$-haloalkyl such as trifluoromethyl, trichloromethyl, 2-chloro-1,1,2-trifluoroethyl and pentafluoroethyl, $C_1$–$C_4$-alkoxy such as methoxy and tert-butoxy, or partly or completely halogenated $C_1$–$C_4$-alkoxy such as trifluoromethoxy, trichloromethoxy, 2-chloro-1,1,2-trifluoroethoxy and pentafluoroethoxy;

a $C_3$–$C_6$-cycloalkenyl group, preferably a $C_5$–$C_6$-cycloalkenyl group, which can be substituted one to three times by halogen such as fluorine, chlorine, bromine and iodine, in particular fluorine and chlorine, or $C_1$–$C_4$-alkyl such as methyl, ethyl and tert-butyl;

$R^3$ is furthermore $C_3$–$C_6$-alkenyl or $C_3$–$C_6$-alkynyl, preferably $C_3$–$C_4$-alkenyl or $C_3$–$C_5$-alkynyl, such as 2-propenyl, 2-butenyl, 2-propynyl, 1,1-dimethyl-2-propynyl and 3-butynyl, which in each case can be substituted one to three times by halogen such as fluorine, chlorine or bromine and/or once by phenyl, it being possible for the phenyl radical in turn to carry one to three of the following substituents: halogen, in particular fluorine and chlorine, cyano, nitro, $C_1$–$C_4$-alkyl such as methyl and tert-butyl, partly or completely halogenated $C_1$–$C_4$-alkyl such as fluoromethyl, trifluoromethyl, trichtoromethyl, 2-chloro-1,1,2-trifluoroethyl and pentafluoroethyl, $C_1$–$C_4$-alkoxy such as methoxy and tertbutoxy, $C_1$–$C_4$-haloalkoxy such as fluoromethoxy, trifluoromethoxy, trichloromethoxy, 2-chloro-1,1,2-trifluoroethoxy and pentafluoroethoxy, $C_1$–$C_4$-alkylthio such as methylthio and tert-butylthio, partly or completely halogenated $C_1$–$C_4$-alkylthio such as fluoromethylthio, trifluoromethylthio, trichloromethylthio, 2-chloro-1,1,2-trifluoroethylthio and pentafluoroethylthio;

$R^3$ is furthermore the phenyl group which can additionally carry one to three of the following radicals: cyano; nitro; halogen such as fluorine, chlorine, bromine and iodine, in particular fluorine and chlorine; $C_1$–$C_6$-alkyl such as mentioned above, in particular methyl, ethyl and 1-methylethyl; partly or completely halogenated $C_1$–$C_6$-alkyl as mentioned above, in particular trifluoromethyl and chlorodifluoromethyl; $C_1$–$C_6$-alkoxy as mentioned above, in particular methoxy and ethoxy; partly or completely halogenated $C_1$–$C_6$-alkoxy as mentioned above, in particular trifluoromethoxy, trichloromethoxy and pentafluoroethoxy; $C_1$–$C_4$-alkylthio as mentioned above, in particular methylthio and ethylthio and/or partly or completely halogenated $C_1$–$C_6$-alkylthio as mentioned above, in particular difluoromethylthio, trifluoromethylthio and pentafluoroethylthio.

The compounds Ia and Ib or the herbicidal compositions containing them can very effectively control broad-leafed weeds and grass weeds in crops such as wheat, rice, maize, soybeans and cotton without damaging the crop plants.

The compounds Ia and Ib or the herbicidal compositions containing them can be applied by spraying, atomizing, dusting, broadcasting or watering, for example in the form of directly sprayable aqueous solutions, powders, suspensions, even high-percentage aqueous, oily or other suspensions or dispersions, emulsions, oil dispersions, pastes, dusting compositions, broadcasting compositions or granules. The application forms depend on the intended uses; in each case they should if possible ensure the finest dispersion of the active compounds according to the invention.

The compounds Ia and Ib are generally suitable for preparing directly sprayable solutions, emulsions, pastes or oil dispersions. Suitable inert additives are mineral oil fractions of medium to high boiling point, such as kerosene or diesel oil, additionally coal tar oils and oils of vegetable or animal origin, aliphatic, cyclic and aromatic hydrocarbons, eg. paraffin, tetrahydronaphthalene, alkylated naphthalenes or their derivatives, alkylated benzenes or their derivatives, methanol, ethanol, propanol, butanol, cyclohexanol, cyclohexanone or strongly polar solvents, such as N-methylpyrrolidone or water.

Aqueous application forms can be prepared from emulsion concentrates, suspensions, pastes, wettable powders or water-dispersible granules by addition of water. To prepare emulsions, pastes or oil dispersions, the substrates as such or dissolved in an oil or solvent can be homogenized in water by means of wetting agents, adhesives, dispersants or emulsifiers. However, concentrates consisting of active substance, wetting agent, adhesive, dispersant or emulsifier and possibly solvent or oil can also be prepared, which are suitable for dilution with water.

Suitable surface-active substances are the alkali metal, alkaline earth metal and ammonium salts of aromatic sulfonic acids, eg. lignosulfonic, phenolsulfonic, naphthalenesulfonic and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols and of fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ether, ethoxylated isooctyl-, octyl- or nonylphenol, alkylphenol or tributylphenyl polyglycol ethers, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the active substances with a solid carrier.

Granules, eg. coated, impregnated and homogeneous granules, can be prepared by binding the active compounds to solid carriers. Solid carriers are mineral earths such as silica gel, silicic acids, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products such as cereal flour, tree bark meal, wood meal and nutshell meal, cellulose powder or other solid carriers.

The formulations in general contain from 0.01 to 95% by weight, preferably from 0.5 to 90% by weight, of active compound. The active compounds are employed here in a purity of from 90% to 100%, preferably from 95% to 100% (by NMR spectrum).

The compounds Ia and Ib according to the invention can be formulated, for example, as follows:

I. 20 parts by weight of the compound No. 2.009 are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

II. 20 parts by weight of the compound No. 2.009 are dissolved solved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

III. 20 parts by weight of the active compound No. 2.009 are dissolved in a mixture which consists of 25 parts by weight of cyclohexanone, 65 parts by weight of a mineral oil fraction of boiling point 210° to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV. 20 parts by weight of the active compound No. 2.009 are well mixed with 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel and the mixture is ground in a hammer mill. By finely dispersing the mixture in 20,000 parts by weight of water, a spray mixture is obtained which contains 0.1% by weight of the active compound.

V. 3 parts by weight of the active compound No. 2.009 are mixed with 97 parts by weight of finely divided kaolin. In this way a dusting composition is obtained which contains 3% by weight of the active compound.

VI. 20 parts by weight of the active compound No. 2.009 are intimately mixed with 2 parts by weight of calcium salt of dodecylbenzenesulfonic acid, 8 parts by weight of fatty alcohol polyglycol ether, 2 parts by weight of sodium salt of a phenol/urea/formaldehyde condensate and 68 parts by weight of a paraffinic mineral oil. A stable oily dispersion is obtained.

The application of the herbicidal compositions or of the active compounds can be carried out pre-emergence or post-emergence. If the active compounds are less tolerable for certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

Depending on the target of control, time of year, target plants and stage of growth, the application rates of active compound are from 0.001 to 3.0, preferably from 0.01 to 2.0, kg/ha of active substance (a.s.).

In consideration of the variety of application methods, the compounds Ia and Ib or compositions containing them can additionally be employed in a further number of crop plants for the elimination of undesired plants. Suitable crops are, for example, the following:

*Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea bataras, Juglans regia, Lens culinaris, Linum usitatissimum, Lycopersicon lycopersicum,* Malus spp., *Manihot esculenta, Medicago sativa,* Musa spp., *Nicotiana tabacum (N. rustica), Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera* and *Zea mays.*

To broaden the spectrum of action and to achieve synergistic effects, the cyanoisoxazoles Ia and Ib can be mixed and applied together with numerous representatives of other herbicidal or growth-regulating active compound groups. For example, suitable mixing components are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which in the 2-position carry, eg. a carboxyl or carbimino group, quinolinecarboxylic acid derivatives, imidazolinones, sulfonamides, sulfonylureas, aryloxy- or heteroaryloxyphenoxypropionic acids and their salts, esters and amides and others.

It may additionally be useful to apply the compounds Ia and Ib on their own, or together, mixed in a combination with other herbicides and additionally with further crop protection agents, for example with agents for controlling pests or phytopathogenic fungi or bacteria. Also of interest is the miscibility with mineral salt solutions, which can be employed for the elimination of nutritional and trace element deficiencies. Non-phytotoxic oils and oil concentrates may also be added.

PREPARATION EXAMPLES

4-Carboxamido-3-isopropylisoxazole-5-carboxylic acid cyclopropylamide 9.9 g of 5-cyclopropylaminocarbonyl-3-isopropylisoxazole-4-carboxylic acid and 9.9 g of thionyl chloride are refluxed in 150 ml of toluene for 1.5 hours. To remove excess thionyl chloride, the mixture is concentrated to dryness, the residue is then taken up again in 50 ml of toluene and this solution is simultaneously added dropwise with 5.7 ml of a 25% strength aqueous ammonia solution at room temperature to an initial amount of 100 ml of toluene. The mixture is stirred for 14 hours, water is then added, and the product which is deposited is filtered off with suction.

Yield: 2.1 g, m.p. 152°–156° C.

The intermediates III shown in Table 1 were synthesized in the same manner:

TABLE 1

III

| No. | $R^1$ | $R^2$ | $R^3$ | m.p. [°C.] |
| --- | --- | --- | --- | --- |
| 1.001 | $CH_3$ | H | $C(CH_3)_3$ | 155–158 |
| 1.002 | $CH(CH_3)_2$ | H | $CH(CH_3)_2$ | 163–165 |
| 1.003 | $CH(CH_3)C_2H_5$ | H | $CH(CH_3)_2$ | 132–134 |
| 1.004 | $C_2H_5$ | H | $CH(CH_3)_2$ | 136–138 |
| 1.005 | $C_2H_5$ | H | $C_3H_5$ | 160–164 |
| 1.006 | $C_2H_5$ | H | $C(CH_3)_3$ | 127–129 |
| 1.007 | $C_2H_5$ | H | $C_6H_5$ | 172–174 |
| 1.008 | $CH(CH_3)_2$ | H | $C_6H_5$ | 148–158 |
| 1.009 | $CH(CH_3)_2$ | H | $3\text{-}CF_3\text{-}C_6H_4$ | 136–139 |
| 1.010 | $CH(CH_3)_2$ | H | $C(CH_3)_2C\equiv CH$ | 114–117 |
| 1.011 | $CH_3$ | H | $CH(CH_3)_2$ | 92–93 |
| 1.012 | $CH_3$ | H | $C(CH_3)_2C\equiv CH$ | 149–151 |

4-Cyano-3-isopropylisoxazole-5-carboxylic acid cyclopropylamide 2.7 g of phosphorus oxychloride are added dropwise at 60° C. to a solution of 2.1 g of 4-carboxamido-3-isopropylisoxazole-5-carboxylic acid cyclopropylamide and 3.7 g of potassium carbonate in 150 ml of acetonitrile. The mixture is then stirred at 70° C. for 4 hours. For working up, the solution is poured onto 200 ml of ice-water, the mixture is extracted with ethyl acetate and the organic phase is then washed with aqueous sodium hydrogen carbonate solution and aqueous sodium chloride solution. The organic phase is dried over magnesium sulfate and freed from the solvent.

Yield: 1.9 g, m.p.: 107°–108° C. (Ex. No. 2.009)

The compounds Ia shown in Table 2 below were obtained in a similar manner:

TABLE 2

Ia

| No. | $R^1$ | $R^2$ | $R^3$ | m.p. [°C.] |
| --- | --- | --- | --- | --- |
| 2.001 | $CH(CH_3)_2$ | H | $C(CH_3)_3$ | 84 |
| 2.002 | $CH(CH_3)C_2H_5$ | H | $CH(CH_3)_2$ | 81–84 |
| 2.003 | $CH(CH_3)_2$ | H | $CH(CH_3)_2$ | 106–108 |
| 2.004 | $C_2H_5$ | H | $CH(CH_3)_2$ | 74–75 |
| 2.005 | $C_2H_5$ | H | $C_3H_5$ | 132–133 |
| 2.006 | $C_2H_5$ | H | $C(CH_3)_3$ | 87–89 |
| 2.007 | $C_2H_5$ | H | $C_6H_5$ | 55 |
| 2.008 | $CH(CH_3)_2$ | H | $C(CH_3)_2C\equiv CH$ | 108–110 |
| 2.009 | $CH(CH_3)_2$ | H | $C_3H_5$ | 107–108 |
| 2.010 | $CH_3$ | H | $CH(CH_3)_2$ | 109–110 |
| 2.011 | $CH_3$ | H | $C(CH_3)_3$ | 110–111 |
| 2.012 | $CH_3$ | H | $C_6H_{11}$ | 130–131 |
| 2.013 | $CH_3$ | H | $C(CH_3)_2C\equiv CH$ | 159–160 |

3-Isopropylisoxazole-4,5-dicarboxylic acid 4-methyl ester 40 g of dimethyl 3-isopropylisoxazole-4,5-dicarboxylate are dissolved in 200 ml of methanol. A solution of 7.05 g of sodium hydroxide in 50 ml of water is added dropwise at 0° C. to this solution. It is stirred for 14 hours and allowed to warm to room temperature. The reaction selution is diluted with water and extracted twice with ethyl acetate. The alkaline solution is then acidified with conc. hydrochloric acid and extracted several times with ethyl acetate, and the organic phase is dried and concentrated.

33.7 g of an oil are obtained, which is employed without further purification.

Methyl 5-carboxamido-3-isopropylisoxazole-4-carboxylate 33.6 g of 3-isopropylisoxazole-4,5-dicarboxylic acid 4-methyl ester and 37.5 g of thionyl chloride are refluxed in 150 ml of toluene for two hours. The mixture is then concentrated to dryness under reduced pressure.

26.8 g of the oil obtained are dissolved in 75 ml of toluene and simultaneously added dropwise with a solution of conc. ammonia (161 ml) to an initial amount of 100 ml of toluene at 0°–10° C. The mixture is stirred at room temperature for 14 hours, water is then added and the resultant precipitate is filtered off with suction.

Yield 15.6 g, m.p. 229°–231° C.

5-Carboxamido-3-isopropylisoxazole-4-carboxylic acid

A solution of 2.9 g of sodium hydroxide in 50 ml of water is added dropwise at 0°–10° C. to a solution of 15.6 g of methyl 5-carboxamido-3-isopropylisoxazole-4-carboxylate in 200 ml of methanol. The mixture is stirred for 14 hours, diluted with water and extracted twice with ethyl acetate, and the aqueous solution is acidified. The oil which is deposited can be taken up in ethyl acetate. After concentrating the organic phase, the desired product is obtained.

Yield 9.1 g, m.p. 150°–152° C.

5-Cyano-3-isopropylisoxazole-4-carboxylic acid cyclopropylamide and 5-carboxamido-3-isopropylisoxazole-4-carboxylic acid cyclopropylamide 9.1 g of 5-carboxamido-3-isopropylisoxazole-4-carboxylic acid and 21.9 g of thionyl chloride are refluxed in 200 ml of toluene for two hours. After concentrating to dryness, 10.6 g of an oil are obtained, which contains 5-cyano-3-isopropylisoxazole-4-carbonyl chloride and 5-carboxamido-3-isopropylisoxazole-4-carbonyl chloride.

3.5 g of this oil are initially taken in 150 ml of toluene and treated at 0°–10° C. with 2.0 g of cyclopropylamine. The mixture is stirred at room temperature for 14 hours, then diluted with water, and the organic phase is separated off and extracted with aqueous sodium hydrogen carbonate solution. The organic phase is concentrated to dryness and 1.8 g of 5-cyano-3-isopropylisoxazole-4-carboxylic acid cyclopropylamide, m.p. 105°–108° C. and 0.6 g of 5-carboxamido-3-isopropylisoxazole-4-carboxylic acid cyclopropylamide, m,p, 130°–134° C. are isolated after chromatography on silica gel (eluent: cyclohexane/ethyl acetate).

The 5-carboxamido compound can be converted to the 5-cyano compound by treatment with thionyl chloride in toluene at reflux temperature.

The intermediates V (Table 3) and the final products Ib (Table 4) were synthesized in the same manner.

TABLE 3

$$\underset{N\diagdown O}{\overset{R^1}{\diagup}}\underset{}{\overset{\overset{O}{\parallel}}{\underset{}{\diagdown}}}\underset{\underset{O}{\parallel}}{\overset{}{\diagup}}\underset{NH_2}{}\quad V$$

| No. | R¹ | R² | R³ | m.p. [°C.] |
|---|---|---|---|---|
| 3.001 | CH(CH₃)₂ | H | CH(CH₃)₂ | 145–153 |
| 3.002 | CH(CH₃)₂ | H | CH(CH₃)₂ | 120–122 |
| 3.003 | C₂H₅ | H | C(CH₃)₃ | 104–106 |
| 3.004 | C₂H₅ | H | C₃H₅ | 151–158 |
| 3.005 | CH₃ | H | C(CH₃)₃ | 141–148 |
| 3.006 | CH₃ | H | CH(CH₃)₂ | 129–131 |
| 3.007 | C₂H₅ | H | CH(CH₃)₂ | 109–118 |
| 3.008 | C₂H₅ | H | C(CH₃)₂C≡CH | 173–176 |
| 3.009 | CH₃ | H | C(CH₃)₂C≡CH | 185–189 |

TABLE 4

$$\underset{N\diagdown O}{\overset{R^1}{\diagup}}\underset{CN}{\overset{CONR^2R^3}{\diagup}}\quad Ib$$

| No. | R¹ | R² | R³ | m.p. [°C.] |
|---|---|---|---|---|
| 4.001 | CH(CH₃)₂ | H | CH(CH₃)₂ | 105–108 |
| 4.002 | CH(CH₃)C₂H₅ | H | CH(CH₃)₂ | 71 |
| 4.003 | CH(CH₃)₂ | H | C₃H₅ | 105–108 |
| 4.004 | CH(CH₃)₂ | H | C(CH₃)₃ | 70–73 |
| 4.005 | CH(CH₃)₂ | H | 3-CF₃—C₆H₄ | 167–169 |
| 4.006 | CH₃ | H | C(CH₃)₃ | oil |

USE EXAMPLES

It was possible to show the herbicidal action of the cyanoisoxazoles of the formula Ia or Ib by greenhouse tests:

The cultivation containers used were plastic flowerpots containing loamy sand containing approximately 3.0% of humus as a substrate. The seeds of the test plants were sown separately according to species.

In the case of pre-emergence treatment, the active compounds suspended or emulsified in water were applied immediately after sowing by means of finely dispersing nozzles. The containers were lightly watered in order to promote germination and growth and then covered with transparent plastic hoods until the plants had taken root. This covering causes uniform germination of the test plants if this has not been adversely affected by the active compounds.

For the purpose of post-emergence treatment, the test plants were first raised to a growth height of 3 to 15 cm depending on growth form and only then treated with the active compounds suspended or emulsified in water. For this purpose, the test plants were either sown directly and then raised in the same containers or they were first raised separately as seed plants and transplanted into the test containers a few days before treatment.

The plants were kept species-specifically at from 10°–25° C. or 20°–35° C. The test period extended over 2 to 4 weeks. During this time, the plants were tended and their reaction to the individual treatments was assessed.

The herbicidal action was graded on a scale of from 0 to 100. 100 in this case means no emergence of the plants or complete destruction of at least the above-ground parts and 0 means no damage or normal course of growth.

The cyano-substituted compounds Ia and Ib showed very good herbicidal action. At the same time, they have a surprisingly advantageous breakdown behavior in the soil. Thus for compound No. 2.009, for example, a half-life $DT_{50}$ of only 1–2 weeks is determined. In contrast, structurally similar compounds from the prior art, eg. comparison substance A, disclosed in EP-A 337 263, are broken down distinctly more slowly. The metabolization tests with A gave a $DT_{50}$ of more than 10 weeks.

No. 2.009

A

Figure 1:
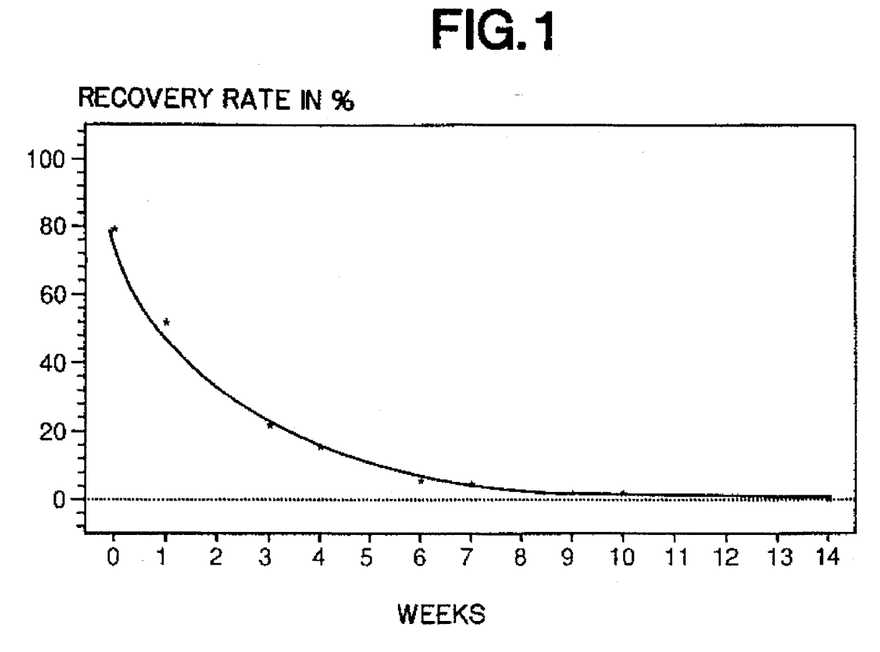
FIG. 1 is a graph showing the breakdown behavior of prior art compound A.
Figure 2:
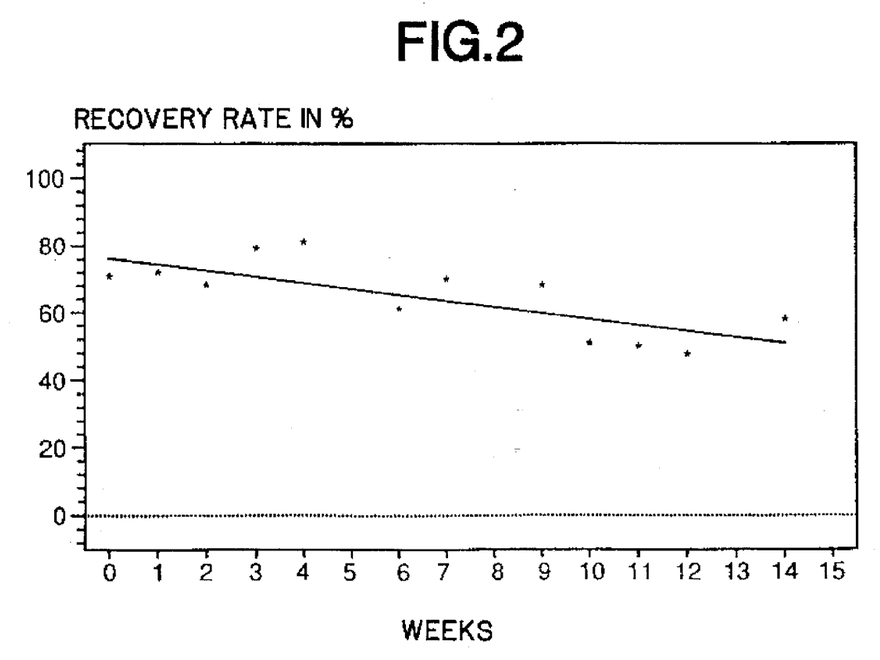
FIG. 2 is agraph showing the breakdown behavior of compound 2.009.

To determine the breakdown behavior, the compounds were added to a mixture of 70% cyclohexane, 20% Nekanil® NL (ethoxylated isooctylphenol) and 10% Emulphor® EC (ethoxylated castor oil) such that the active compound content was 100 g/l. 113.4 μl of the active compound formulated in this way were dissolved in 100 ml of double-distilled water and of this 1 ml in each case was added to a defined amount weighed in a plastic bag (weight per bag in each case based on 100 g dry weight of the soil) of biologically active field soil (properties: loamy sand; pH 6.1; humus 1.2%, cation exchange capacity 4.8 meq of Ba/100 g of soil). This gives an application rate of 0.6 kg of a.s./ha. By addition of a calculated amount of water, the soil was adjusted to 40% of its max. water capacity and the samples of active substance, field soil and water thus prepared were well mixed and stored at 20° C. During the test period (30.09.93–06.01.94), soil samples were extracted with methanol and the metabolization rate was determined by means of HPLC. The test results can be taken from FIGS. 1 and 2.

We claim:
1. A cyanoisoxazole of the formula Ia or Ib where
$R^1$ is
hydrogen;
$C_1$–$C_6$-alkyl optionally substituted by one to five halogen atoms and/or one cyano radical and/or up to two of the following radicals: $C_1$–$C_4$-alkoxy, $C_1$–$C_4$-haloalkoxy, $C_1$–$C_4$-alkylthio, $C_1$–$C_4$-haloalkylthio, $C_3$–$C_6$-cycloalkyl, optionally substituted by one to three halogen or $C_1$–$C_4$-alkyl radicals or phenyl optionally additionally substituted by one to three of the following radicals: cyano, halogen, nitro, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio;
$C_3$–$C_8$-cycloalkyl otionally substituted one to three times by $C_1$–$C_4$-alkyl and/or halogen;
phenyl optionally substituted by one to three of the following radicals: cyano, nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio;
$R^2$ is
hydrogen;
$C_1$–$C_6$-alkyl optionally substituted by one to three of the following substituents: hydroxyl, halogen, $C_1$–$C_4$-alkoxy and/or $C_1$–$C_4$-alkylthio;
$C_3$–$C_8$-cycloalkyl optionally substituted one to three times by halogen, $C_1$–$C_4$-alkyl and/or $C_1$–$C_4$-haloalkyl;
$R^3$ is
a $C_1$–$C_4$-alkoxy group;
a $C_1$–$C_6$-alkyl group optionally substituted by one to three of the following radicals: halogen, cyano, $C_1$–$C_4$-alkoxy, $C_1$–$C_4$-haloalkoxy, $C_1$–$C_4$-alkylthio, $C_1$–$C_4$-haloalkylthio, $C_3$–$C_8$-cycloalkyl or phenyl optionally substituted by one to three of the following radicals: halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and/or $C_1$–$C_4$-haloalkylthio;
a $C_3$–$C_6$-cycloalkyl group optionally substituted one to three times by halogen or $C_1$–$C_4$-alkyl;
A $C_3$–$C_8$-cycloalkyl group optionally substituted by one to three of the following radicals: halogen, nitro, cyano, $C_1$–$C_6$-alkyl, $C_1$–$C_6$-haloalkyl, $C_1$–$C_4$-alkoxy and/or $C_1$–$C_4$-haloalkoxy;
a $C_3$–$C_6$-alkenyl or $C_3$–$C_6$-alkynyl group each of which is optionally substituted one to three times by halogen and/or once by phenyl optionally substituted by one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro;
the phenyl group optionally substituted by one to three of the following radicals: cyano, nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio and/or $C_1$–$C_6$-haloalkylthio.

2. A composition containing inert carriers and a herbicidally active amount of at least one cyanoisoxazole of the formula Ia or Ib as defined in claim 1.

3. A method for controlling undesired plant growth, which comprises treating the undesired plants and/or their habitat with a herbicidally active amount of a cyanoisoxazole of the formula Ia or Ib as defined in claim 1.

* * * * *

UNITED STATES PATENT AND TRADEMARK OFFICE
CERTIFICATE OF CORRECTION

PATENT NO.: 5,543,416

DATED: August 6, 1996

INVENTOR(S): MUENSTER et al.

It is certified that error appears in the above-identified patent and that said Letters Patent is hereby corrected as shown below:

Title page, item [57], "ABSTRACT" should read --ABSTRACT OF THE DISCLOSURE--.

Column 15, claim 1, line 27, "$C_1$-$C_6$-haloalkoxy" should read --$C_1$-$C_6$-haloalkoxy--.

Signed and Sealed this

Twenty-second Day of October, 1996

Attest:

BRUCE LEHMAN

Attesting Officer

Commissioner of Patents and Trademarks